US012790585B2

(12) United States Patent
Sakuma et al.

(10) Patent No.: US 12,790,585 B2
(45) Date of Patent: Nov. 10, 2026

(54) MATURATION AGENT

(71) Applicant: Orizuru Therapeutics, Inc., Fujisawa (JP)

(72) Inventors: Kensuke Sakuma, Kanagawa (JP); Hirokazu Matsumoto, Kanagawa (JP); Taro Toyoda, Kyoto (JP); Shuhei Konagaya, Kyoto (JP)

(73) Assignee: Orizuru Therapeutics, Inc., Kanagawa (JP)

( * ) Notice: Subject to any disclaimer, the term of this patent is extended or adjusted under 35 U.S.C. 154(b) by 752 days.

(21) Appl. No.: 18/033,961

(22) PCT Filed: Nov. 19, 2021

(86) PCT No.: PCT/JP2021/042557

§ 371 (c)(1),
(2) Date: Apr. 26, 2023

(87) PCT Pub. No.: WO2022/107877

PCT Pub. Date: May 27, 2022

(65) Prior Publication Data

US 2023/0399607 A1 Dec. 14, 2023

(30) Foreign Application Priority Data

Nov. 20, 2020 (JP) ................................ 2020-193454

(51) Int. Cl.
*C12N 5/071* (2010.01)
*C12N 5/00* (2006.01)

(52) U.S. Cl.
CPC ......... *C12N 5/0602* (2013.01); *C12N 5/0018* (2013.01); *C12N 2501/999* (2013.01); *C12N 2506/22* (2013.01)

(58) Field of Classification Search
CPC ................ C12N 5/0602; C12N 5/0018; C12N 2501/999; C12N 2506/22; C12N 2501/405; C12N 2506/45; C12N 5/0676
See application file for complete search history.

(56) References Cited

U.S. PATENT DOCUMENTS

2011/0014703 A1 1/2011 Xu et al.
2014/0186953 A1 7/2014 Rezania
(Continued)

FOREIGN PATENT DOCUMENTS

CA 3097962 A1 * 10/2019 ............. A61K 35/39
CN 102597219 A 7/2012
(Continued)

OTHER PUBLICATIONS

Hofmann et al., Selective and Potent CDK8/19 Inhibitors Enhance NK-Cell Activity and Promote Tumor Surveillance. Mol Cancer Ther. Apr. 2020;19(4):1018-1030 (Year: 2020).*
(Continued)

*Primary Examiner* — Tracy Vivlemore
*Assistant Examiner* — Thomas R. Amick
(74) *Attorney, Agent, or Firm* — Foley & Lardner LLP

(57) ABSTRACT

An object of the present invention is to provide a novel method for inducing the differentiation of pluripotent stem cells into an insulin-positive cell population. The present invention provides a method for producing an insulin-positive cell population, comprising differentiating a pancreatic progenitor cell population or a cell population at a later stage of differentiation in a medium containing a CDK8/19 inhibitor.

10 Claims, 2 Drawing Sheets

(56) References Cited

U.S. PATENT DOCUMENTS

| | | | |
|---|---|---|---|
| 2016/0000787 A1 | 1/2016 | Broude et al. |
| 2019/0367882 A1 | 12/2019 | Wells et al. |
| 2019/0390169 A1 | 12/2019 | Osafune et al. |
| 2021/0060210 A1 | 3/2021 | Toyoda et al. |
| 2021/0292708 A1 | 9/2021 | Yamazoe et al. |
| 2021/0353686 A1 | 11/2021 | Ito et al. |
| 2022/0168357 A1 | 6/2022 | Hiyoshi et al. |

FOREIGN PATENT DOCUMENTS

| | | | |
|---|---|---|---|
| CN | 111868235 | A | 10/2020 |
| JP | 2016-503654 | A | 2/2016 |
| WO | WO-2016/100782 | A1 | 6/2016 |
| WO | WO-2018/159805 | A1 | 9/2018 |
| WO | WO-2020/027316 | A1 | 2/2020 |
| WO | WO-2020/059892 | A1 | 3/2020 |
| WO | WO-2020/209389 | A1 | 10/2020 |

OTHER PUBLICATIONS

Lynch et al., "Global hyperactivation of enhancers stabilized human and mouse naive pluripotency through inhibition of CDK8/19 Mediator kinases," Nature Cell Biology, Oct. 2020 (online Sep. 28, 2020), 22(10):1223-1238.

Supplementary European Search Report dated Jan. 17, 2025 in EP 21894748.9.

Konagaya et al., "Expansion of pluripotent stem cell-derived pancreatic progenitor cells," Programs and Abstracts of the 44th Annual Congress of Japanese Pancreas and Islet Transplantation Association, 2017, O-29, p. 82, with English translation.

Konagaya et al., "Large-scale preparation of human iPS cell-derived pancreatic islet cellss," Preprints of the 36th Annual Meeting of the Japanese Society for Biomaterials, 2017, IC-10, p. 77, with English translation.

Toyoda et al., "Cell aggregation optimizes the differentiation of human ESCs and iPSCs into pancreatic bud-like progenitor cells," Stem Cell Research, Jan. 28, 2015, 14(2):185-197.

Toyoda et al., "Efforts toward the Development of Human IPS Cell-Derived Pancreatic Islets," Programs and Abstracts of the 46th Annual Congress of Japanese Pancreas and Islet Transplantation Association, 2019, p. 47, with English translation.

Toyoda et al., "Up to Date on Pancreatic Regeneration," Nephrology, Sep. 28, 2020, 12(3):329-336, with English translation.

International Search Report dated Jan. 25, 2022 in PCT/JP2021/042557.

Office Action and Search Report dated Aug. 21, 2026 in CN 202180075398.8.

* cited by examiner

MATURATION AGENT

CROSS-REFERENCE TO RELATED APPLICATIONS

This application is the U.S. National Stage of PCT/JP2021/042557, filed Nov. 19, 2021, which claims priority to JP 2020-193454, filed Nov. 20, 2020.

TECHNICAL FIELD

The present invention relates to a method for producing an insulin-positive cell population from pluripotent stem cells. More specifically, the present invention relates to a method for producing an insulin-positive cell population, comprising allowing a factor having inhibitory activity for cyclin-dependent kinase 8 and/or cyclin-dependent kinase 19 (hereinafter, also referred to as "CDK8/19") to act on a pancreatic progenitor cell population or a cell population at a later stage of differentiation obtained by the induction of differentiation from pluripotent stem cells.

BACKGROUND ART

Research is underway to induce the differentiation of pluripotent stem cells such as iPS cells or ES cells into insulin-positive cells or pancreatic β cells and to apply the obtained cells to the treatment of diabetes mellitus.

Various approaches have been developed and reported so far in order to induce the differentiation of pluripotent stem cells into insulin-positive cell populations (Non Patent Literature 1). However, an insulin-positive cell population obtained by the induction of differentiation comprises various cells in addition to the insulin-positive cells (particularly, insulin-positive and NKX6.1-positive cells, etc.) of interest. In the case of applying an insulin-positive cell population to the treatment of diabetes mellitus, it is very important from a safety standpoint to strictly control the types of cells contained in the cell population. Hence, there has been a strong demand for a novel method for inducing differentiation into an insulin-positive cell population comprising a higher proportion of the cells of interest.

CITATION LIST

Non Patent Literature

Non Patent Literature 1: Stem Cell Research (2015) 14, 185-197

SUMMARY OF INVENTION

Technical Problem

An object of the present invention is to provide a novel method for inducing the differentiation of pluripotent stem cells into an insulin-positive cell population.

Solution to Problem

The present inventors have conducted diligent studies to attain the object and consequently found that in the process of inducing an insulin-positive cell population from pluripotent stem cells, a factor having CDK8/19-inhibiting activity (hereinafter, also referred to as a "CDK8/19 inhibitor") is allowed to act on a pancreatic progenitor cell population or a cell population at a later stage of differentiation, whereby differentiation into insulin-positive cells, particularly, insulin-positive and NKX6.1-positive cells, can be efficiently induced and an insulin-positive cell population comprising a higher proportion of the cells can be obtained as compared with a conventional method.

The present invention is based on these novel findings and encompasses the following inventions.

[1] A method for producing an insulin-positive cell population, comprising
differentiating a pancreatic progenitor cell population or a cell population at a later stage of differentiation in a medium containing a CDK8/19 inhibitor.

[2] The method according to [1], wherein the medium has substantially no ALK5-inhibiting activity.

[3] The method according to [1] or [2], wherein IC 50 of the CDK8/19 inhibitor against ALK5 is 1 μM or more.

[4] The method according to any of [1] to [3], wherein the CDK8/19 inhibitor is one or more selected from the group consisting of diethyl (E)-(4-(3-(5-(4-fluorophenyl)-1-methyl-1H-pyrazol-4-yl)acrylamido)benzyl) phosphonate, 2-(4-(4-(isoquinolin-4-yl)phenyl)-1H-pyrazol-1-yl)-N,N-dimethylacetamide, 4-((2-(6-(4-methylpiperazine-1-carbonyl)naphthalen-2-yl)ethyl) amino)quinazoline-6-carbonitrile, 4-(4-(2,3-dihydrobenzo[b][1,4]dioxin-6-yl)-1H-pyrazol-3-yl) benzene-1,3-diol, 3-(2-(imidazo[1,2-b]pyridazin-6-ylthio)ethyl)-4-(naphthalen-1-ylsulfonyl)-3,4-dihydroquinoxalin-2(1H)-one, and (E)-3-(4-(1-cyclopropyl-1H-pyrazol-4-yl)pyridin-3-yl)-N-(4-(morpholinomethyl)phenyl)acrylamide.

[5] The method according to any of [1] to [4], wherein the pancreatic progenitor cell population or the cell population at a later stage of differentiation is a cell population produced by the induction of differentiation from pluripotent stem cells.

[6] A differentiation medium for a pancreatic progenitor cell population or a cell population at a later stage of differentiation, comprising a CDK8/19 inhibitor.

[7] The medium according to [6], wherein the medium has substantially no ALK5-inhibiting activity.

[8] The medium according to [6] or [7], wherein IC 50 of the CDK8/19 inhibitor against ALK5 is 1 μM or more.

[9] The medium according to any of [6] to [8], wherein the CDK8/19 inhibitor is one or more selected from the group consisting of diethyl (E)-(4-(3-(5-(4-fluorophenyl)-1-methyl-1H-pyrazol-4-yl)acrylamido)benzyl) phosphonate, 2-(4-(4-(isoquinolin-4-yl)phenyl)-1H-pyrazol-1-yl)-N,N-dimethylacetamide, 4-((2-(6-(4-methylpiperazine-1-carbonyl)naphthalen-2-yl)ethyl) amino)quinazoline-6-carbonitrile, 4-(4-(2,3-dihydrobenzo[b][1,4]dioxin-6-yl)-1H-pyrazol-3-yl) benzene-1,3-diol, 3-(2-(imidazo[1,2-b]pyridazin-6-ylthio)ethyl)-4-(naphthalen-1-ylsulfonyl)-3,4-dihydroquinoxalin-2(1H)-one, and (E)-3-(4-(1-cyclopropyl-1H-pyrazol-4-yl)pyridin-3-yl)-N-(4-(morpholinomethyl)phenyl)acrylamide.

The present specification encompasses the contents described in the specification and/or drawings of Japanese Patent Application No. 2020-193454 filed on Nov. 20, 2020 on which the priority of the present application is based.

All publications, patents and patent applications cited herein are incorporated herein by reference in their entirety.

Advantageous Effects of Invention

The present invention can provide a novel method for inducing the differentiation of pluripotent stem cells into an insulin-positive cell population. Specifically, the present invention enables differentiation into insulin-positive cells, particularly, insulin-positive and NKX6.1-positive cells, to be efficiently induced in the process of inducing an insulin-positive cell population from pluripotent stem cells, and enables an insulin-positive cell population comprising a higher proportion of the cells to be obtained as compared with a conventional method.

DESCRIPTION OF EMBODIMENTS

1. Terminology

Figure 1:
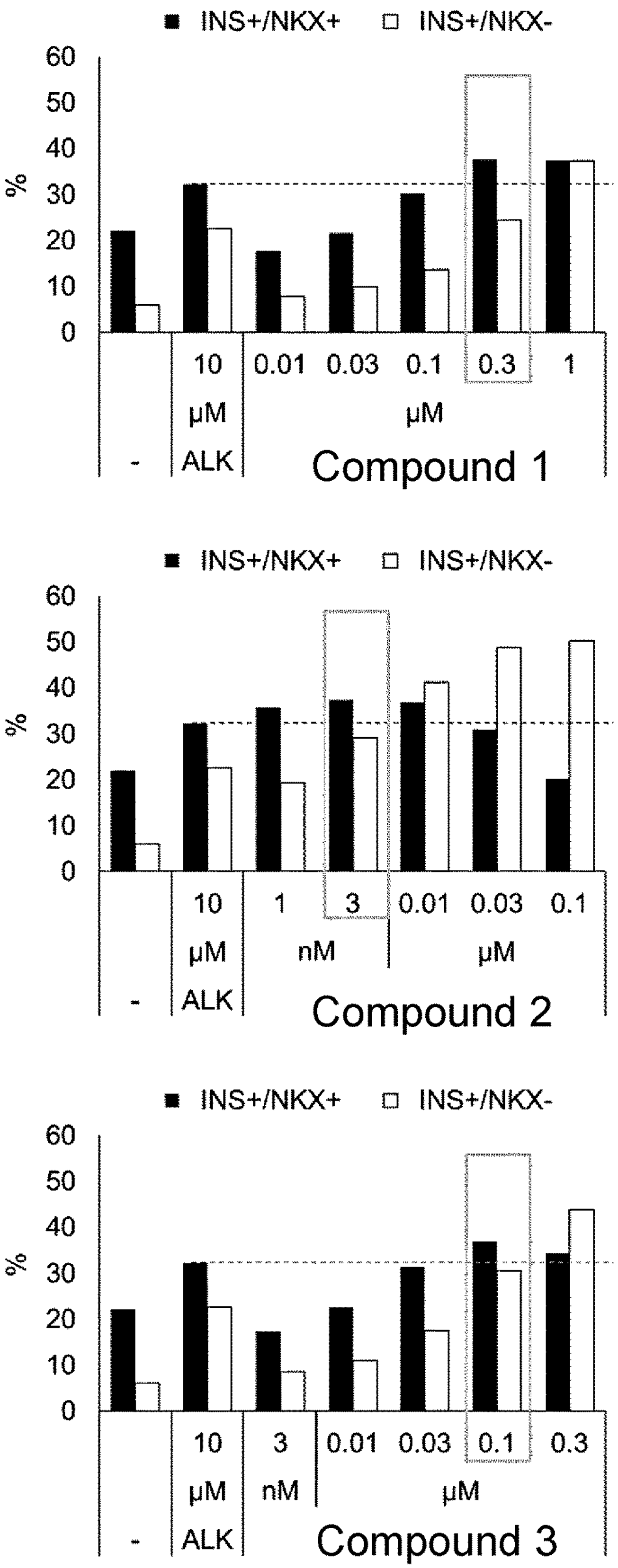
FIG. 1 is a graph diagram showing the proportion of insulin-positive and NKX6.1-positive (indicated by "INS+/NKX+") cells and the proportion of insulin-positive and NKX6.1-negative (indicated by "INS+/NKX−") cells in an insulin-positive cell population obtained by treating a pancreatic progenitor cell population with a medium for induction of differentiation containing ALK5 inhibitor II or a CDK8/19 inhibitor (compound 1, compound 2 or compound 3).

Hereinafter, the terms described herein will be described.

As used herein, "about" or "around" refers to a value which may vary up to plus or minus 25%, 20%, 10%, 8%, 6%, 5%, 4%, 3%, 2%, or 1% from the reference value. Preferably, the term "about" or "around" refers to a range from minus or plus 15%, 10%, 5%, or 1% from the reference value.

As used herein, "comprise(s)" or "comprising" means inclusion of the element(s) following the word without limitation thereto. Accordingly, it indicates inclusion of the element(s) following the word, but does not indicate exclusion of any other element.

As used herein, "consist(s) of" or "consisting of" means inclusion of all the element(s) following the phrase and limitation thereto. Accordingly, the phrase "consist(s) of" or "consisting of" indicates that the enumerated element(s) is required or essential and substantially no other elements exist.

As used herein, "without the use of feeder cell(s)" means basically containing no feeder cells and using no medium preconditioned by culturing feeder cells. Accordingly, the medium does not contain any substance, such as a growth factor or a cytokine, secreted by feeder cells.

"Feeder cells" or "feeder" means cells that are co-cultured with another kind of cells, support the cells, and provide an environment that allows the cells to grow. The feeder cells may be derived from the same species as or a different species from the cells that they support. For example, as a feeder for human cells, human skin fibroblasts or human embryonic-stem cells may be used or a primary culture of murine embryonic fibroblasts or immortalized murine embryonic fibroblasts may be used. The feeder cells can be inactivated by exposure to radiation or treatment with mitomycin C.

As used herein, "adhered (adherent)" refers to cells are attached to a container, for example, cells are attached to a cell culture dish or a flask made of a sterilized plastic (or coated plastic) in the presence of an appropriate medium. Some cells cannot be maintained or grow in culture without adhering to the cell culture container. In contrast, non-adherent cells can be maintained and proliferate in culture without adhering to the container.

As used herein, "culture" refers to maintaining, growing, and/or differentiating cells in in vitro environment. "Culturing" means maintaining, proliferating, and/or differentiating cells out of tissue or the living body, for example, in a cell culture dish or flask. The culture includes two-dimensional culture (plane culture) and three-dimensional culture (suspension culture).

As used herein, "enrich(es)" and "enrichment" refer to increasing the amount of a certain component in a composition such as a composition of cells and "enriched" refers, when used to describe a composition of cells, for example, a cell population, to a cell population increased in the amount of a certain component in comparison with the percentage of such component in the cell population before the enrichment. For example, a composition such as a cell population can be enriched for a target cell type and, accordingly, the percentage of the target cell type is increased in comparison with the percentage of the target cells present in the cell population before the enrichment. A cell population can be enriched for a target cell type by a method of selecting and sorting cells known in the art. A cell population can be enriched by a specific process of sorting or selection described herein. In a certain embodiment of the present invention, a cell population is enriched for a target cell population at least 20%, 30%, 40%, 50%, 60%, 70%, 80%, 85%, 90%, 95%, 97%, 98%, or 99% by a method of enriching the target cell population.

As used herein, "deplete(s)" and "depletion" refer to decreasing the amount of a certain component in a composition such as a composition of cells and "depleted" refers, when used to describe a composition of cells, for example, a cell population, to a cell population decreased in the amount of a certain component in comparison with the percentage of such component in the cell population before the depletion. For example, a composition such as a cell population can be depleted for a target cell type and, accordingly, the percentage of the target cell type is decreased in comparison with the percentage of the target cells present in the cell population before the depletion. A cell population can be depleted for a target cell type by a method of selecting and sorting cells known in the art. A cell population can be depleted by a specific process of sorting or selection described herein. In a certain embodiment of the present invention, a cell population is reduced (depleted) for a target cell population at least 50%, 80%, 85%, 90%, 95%, 97%, 98%, or 99% by a method of depleting a target cell population.

As used herein, "purify(ies)" and "purification" refer to removing impurities in a composition such as a composition of cells and making it pure for a certain component and "purified" refers, when used to describe a composition of cells, for example, a cell population, to a cell population in which the amount of impurities is decreased in comparison with the percentage of such components in the cell population before purification and the purity of a certain component is improved. For example, a composition such as a cell population can be purified for a target cell type and, accordingly, the percentage of the target cell type is increased in comparison with the percentage of the target cells present in the cell population before the purification. A cell population can be purified for a target cell type by a method of selecting and sorting cells known in the art. A cell population can be purified by a specific process of sorting or selection described herein. In a certain embodiment of the present invention, the purity of a target cell population is brought by a method of purifying a target cell population to at least 70%, 80%, 85%, 90%, 95%, 97%, 98%, or 99% or to the extent at which impurities (including contaminant cells) are undetectable.

As used herein, "marker" means a cell antigen or a gene thereof that is specifically expressed depending on a predetermined cell type, such as "marker protein" and "marker gene". Preferably, a marker is a cell surface marker and this allows concentration, isolation, and/or detection of living cells. A marker can be a positive selection marker or a negative selection marker.

The detection of a marker protein can be conducted by an immunological assay, for example, ELISA, immunostaining, or flow cytometry using an antibody specific for the marker protein. The detection of a marker gene can be conducted by a method of amplifying and/or detecting nucleic acid known in the art, for example, RT-PCR, microarray, biochip, or the like. As used herein, "positive" for a marker protein means being detected to be positive by flow cytometry and "negative" therefor means being equal to or less than the lower detection limit in flow cytometry. Also, as used herein, "positive" for a marker gene means being detected by RT-PCR and "negative" therefor means being equal to or less than the lower detection limit in RT-PCR.

As used herein, "expression" is defined as transcription and/or translation of a certain nucleotide sequence driven by an intracellular promoter.

As used herein, "factor having CDK8/19-inhibiting activity" or "CDK8/19 inhibitor" means any substance having the inhibitory activity for CDK8/19. CDK8, in contrast to the other proteins of the same CDK family, is not required for cell proliferation. The inhibition of CDK8 has no great effect under usual conditions. CDK19 and CDK8 are similar to each other. Usually, the inhibition of CDK8 also involves the inhibition of CDK19.

As used herein, "growth factors" are endogenous proteins that promote differentiation and/or proliferation of particular cells. Examples of "growth factors" include epidermal growth factor (EGF), acid fibroblast growth factor (aFGF), basic fibroblast growth factor (bFGF), hepatocyte growth factor (HGF), insulin-like growth factor 1 (IGF-1), insulin-like growth factor 2 (IGF-2), keratinocyte growth factor (KGF), nerve growth factor (NGF), platelet-derived growth factor (PDGF), transformation growth factor beta (TGF-β), vascular endothelial growth factor (VEGF), transferrin, various interleukins (for example, IL-1 to IL-18), various colony stimulating factors (for example, granulocyte/macrophage-colony stimulating factor (GM-CSF)), various interferons (for example, IFN-γ, and the like), and other cytokines having effects on stem cells, for example, stem cell factor (SCF), and erythropoietin (Epo).

As used herein, "ROCK inhibitors" means substances that inhibit Rho kinase (ROCK: Rho-associated, coiled-coil containing protein kinase) and may be substances that inhibit either of ROCK I and ROCK II. The ROCK inhibitors are not particularly limited as long as they have the aforementioned function and examples include N-(4-pyridinyl)-4β-[(R)-1-aminoethyl]cyclohexane-la-carboxamide (that may be herein also referred to as Y-27632), Fasudil (HA1077), (2S)-2-methyl-1-[(4-methyl-5-isoquinolinyl]sulfonyl]hexahydro-1H-1,4-diazepine (H-1152), 4β-[(1R)-1-aminoethyl]-N-(4-pyridyl)benzene-1α-carbamide (Wf-536), N-(1H-pyrrolo[2,3-b]pyridin-4-yl)-4PER(R)-1-aminoethyl] cyclohexane-1α-carboxamide (Y-30141), N-(3-{[2-(4-amino-1,2,5-oxadiazol-3-yl)-1-ethyl-1H-imidazo[4,5-c] pyridin-6-yl]oxy}phenyl)-4-{[2-(4-morpholinyl)ethyl]-oxy}benzamide (GSK269962A), N-(6-fluoro-1H-indazol-5-yl)-6-methyl-2-oxo-4-[4-(trifluoromethyl)phenyl]-3,4-dihydro-1H-pyridine-5-carboxamide (GSK429286A). The ROCK inhibitors are not limited to these and antisense oligonucleotides and siRNA to ROCK mRNA, antibodies that bind to ROCK, and dominant negative ROCK mutants can also be used, commercially available, or synthesized according to a known method as ROCK inhibitors.

As used herein, "GSK3β inhibitors" are substances having the inhibitory activity for GSK3β (glycogen synthase kinase 3β). GSK3 (glycogen synthase kinase 3) is a serine/threonine protein kinase and involved in many signaling pathways associated with the production of glycogen, apoptosis, maintenance of stem cells, etc. GSK3 has the 2 isoforms α and β. "GSK3β inhibitors" used in the present invention are not particularly limited as long as they have the GSK3β-inhibiting activity and they may be substances having both the GSK3α-inhibiting activity and the GSK3β-inhibiting activity.

Examples of GSK3β inhibitors include CHIR98014 (2-[[2-[(5-nitro-6-aminopyridin-2-yl)amino]ethyl]amino]-4-(2,4-dichlorophenyl)-5-(1H-imidazol-1-yl)pyrimidine), CHIR99021 (6-[[2-[[4-(2,4-dichlorophenyl)-5-(4-methyl-1H-imidazol-2-yl)-2-pyrimidinyl]amino]ethyl]amino]nicotinonitrile), TDZD-8 (4-benzyl-2-methyl-1,2,4-thiadiazolidine-3,5-dione), SB216763 (3-(2,4-dichlorophenyl)-4-(1-methyl-1H-indol-3-yl)-1H-pyrrole-2,5-dione), TWS-119 (3-[6-(3-aminophenyl)-7H-pyrrolo[2,3-d]pyrimidin-4-yloxy] phenol), kenpaullone, 1-azakenpaullone, SB216763 (3-(2,4-dichlorophenyl)-4-(1-methyl-1H-indol-3-yl)-1H-pyrrole-2,5-dione), SB415286 (3-[(3-chloro-4-hydroxyphenyl) amino]-4-(2-nitrophenyl)-1H-pyrrole-2,5-dione), and AR-A0144-18, CT99021, CT20026, BIO, BIO-acetoxime, pyridocarbazole-ruthenium cyclopentadienyl complex, OTDZT, alpha-4-dibromoacetophenone, lithium, and the like. GSK3β is not limited to these and antisense oligonucleotides and siRNA to GSK3β mRNA, antibodies that bind to GSK3β, dominant negative GSK3β mutants, and the like can also be used, commercially available, or synthesized according to a known method as GSK3β inhibitors.

As used herein, examples of "serum replacement" include KnockOut™ Serum Replacement (KSR: Thermo Fisher Scientific), StemSure® Serum Replacement (Wako), B-27 supplement, N2-supplement, albumin (for example, lipid rich albumin), insulin, transferrin, fatty acids, collagen precursors, trace elements (for example, zinc, selenium (for example, sodium selenite)), 2-mercaptoethanol, 3'-thiolglycerol, or mixtures thereof (for example, ITS-G). Preferred serum replacements are B-27 supplement, KSR, StemSure® Serum Replacement, ITS-G. The concentration of serum replacement in a medium when added into a medium is 0.01-10% by weight, and preferably 0.1-2% by weight. In the present invention, "serum replacement" is preferably used instead of serum.

2. Method for Producing Insulin-Positive Cell Population

The present invention provides a method for producing an insulin-positive cell population, comprising differentiating a pancreatic progenitor cell population or a cell population at a later stage of differentiation in the presence of a CDK8/19 inhibitor.

The CDK8/19 inhibitor acts on a pancreatic progenitor cell population or a cell population at a later stage of differentiation to give rise to an insulin-positive cell population enriched in insulin-positive cells, particularly, insulin-positive and NKX6.1-positive cells.

"CDK8/19 inhibitor" used in the present invention is not particularly limited as long as the CDK8/19 inhibitor has CDK8/19-inhibiting activity. Any factor that directly or indirectly inhibits the function of CDK8/19 can be used. Preferably, "CDK8/19 inhibitor" according to the present invention refers to a factor that inhibits 50% or more of CDK8/19. A method for examining the presence or absence of CDK8/19-inhibiting activity can be selected from known methods. Examples thereof include a method of Example 1 herein described below in detail.

In the present invention, conventionally known "CDK8/19 inhibitor" can be used, and such a CDK8/19 inhibitor can be found from patent literatures or non patent literatures. For example, among compounds described in US2012/0071477, WO2015/159937, WO2015/159938, WO2013/116786, WO2014/0038958, WO2014/134169, JP2015/506376, US2015/0274726, US2016/0000787, WO2016/009076, WO2016/0016951, WO2016/018511, WO2016/100782 and WO2016/182904, a compound (or a salt thereof) having CDK8/19-inhibiting activity can be used as "CDK8/19 inhibitor" according to the present invention. Among the compounds described above, particularly, a compound (or a salt thereof) having activity of selectively inhibiting CDK8/19 can be suitably used.

When "CDK8/19 inhibitor" has inhibitory activity for ALK5 (activin receptor-like kinase 5), the concentration of the CDK8/19 inhibitor necessary for exhibiting an inhibition rate of 50% (IC H value) against ALK5 is preferably 1 μM or more. Use of such a CDK8/19 inhibitor enables a medium supplemented with the CDK8/19 inhibitor to have substantially no ALK5-inhibiting activity. "Have substantially no ALK5-inhibiting activity" not only means that the medium has no ALK5-inhibiting activity but includes the case where the inhibition rate against ALK5 is less than 50%, preferably 40% or less, more preferably 30% or less, further preferably 20% or less, still further preferably 10% or less, especially preferably 5% or less.

More specifically, examples of the CDK8/19 inhibitor that may be used in the present invention include, but are not particularly limited to, compounds given below and salts thereof. These compounds may have one or more substituents or their substructures (substituents, rings, etc.) may be partially converted as long as the compounds have CDK8/19-inhibiting activity.

TABLE 1

| Compound | IUPAC name | Structural formula |
|---|---|---|
| 1 | Diethyl (E)-(4-(3-(5-(4-fluorophenyl)-1-methyl-1H-pyrazol-4-yl)acrylamido)benzyl)phosphonate | 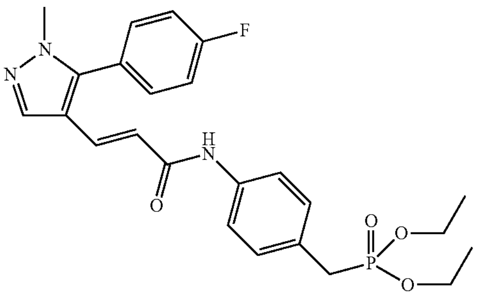 [SMILES: CCOP(=O)(Cc1ccc(NC(=O)/C=C/c2cnn(C)c2-c2ccc(F)cc2)cc1)OCC] |
| 2 | 2-(4-(4-(Isoquinolin-4-yl)phenyl)-1H-pyrazol-1-yl)-N,N-dimethylacetamide | 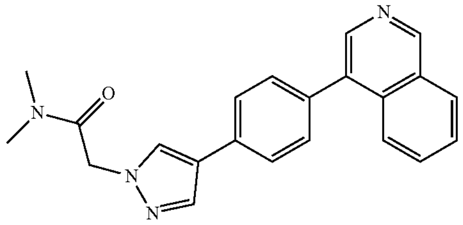 [SMILES: CN(C)C(=O)Cn1cc(-c2ccc(-c3cncc4ccccc34)cc2)cn1] |
| 3 | 4-((2-(6-(4-Methylpiperazine-1-carbonyl)naphthalen-2-yl)ethyl)amino)quinazoline-6-carbonitrile | 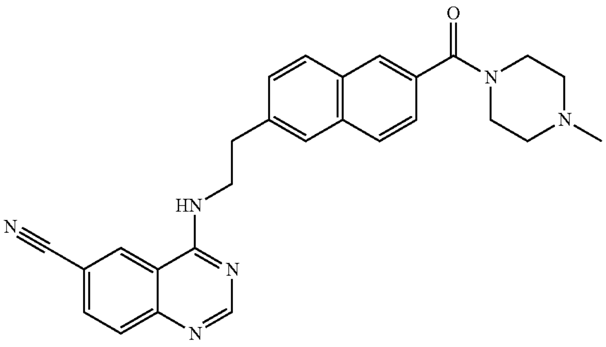 [SMILES: CN1CCN(C(=O)c2ccc3cc(CCNc4ncnc5ccc(C#N)cc45)ccc3c2)CC1] |

TABLE 1-continued

| Compound | IUPAC name | Structural formula |
|---|---|---|
| 4 | 4-(4-(2,3-Dihydrobenzo[b][1,4]dioxin-6-yl)-1H-pyrazol-3-yl)benzene-1,3-diol | 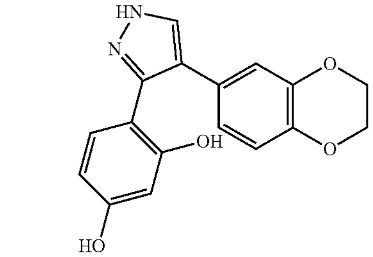 [SMILES: Oc1ccc(-c2n[nH]cc2-c2ccc3c(c2)OCCO3)c(O)c1] |
| 5 | 3-(2-(Imidazo[1,2-b]pyridazin-6-ylthio)ethyl)-4-(naphthalen-1-ylsulfonyl)-3,4-dihydroquinoxalin-2(1H)-one | 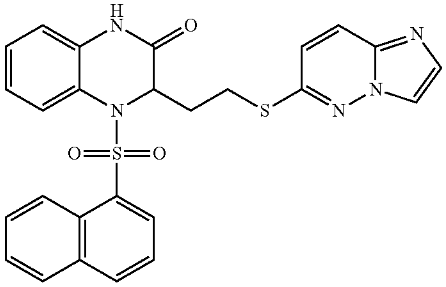 [SMILES: O=C1Nc2ccccc2N(S(=O)(=O)c2cccc3ccccc23)C1CCSc1ccc2nccn2n1] |
| 6 | (E)-3-(4-(1-Cyclopropyl-1H-pyrazol-4-yl)pyridin-3-yl)-N-(4-(morpholinomethyl)phenyl)acrylamide | 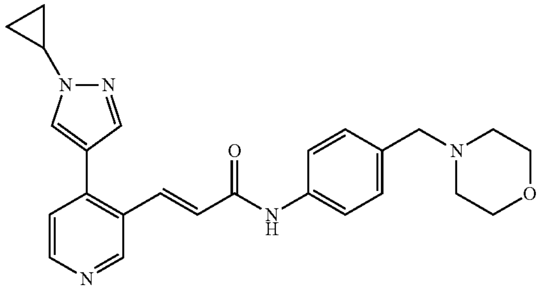 [SMILES: O=C(/C=C/c1cnccc1-c1cnn(C2CC2)c1)Nc1ccc(CN2CCOCC2)cc1] |

Examples of the CDK8/19 inhibitor that may be used in the present invention can include, but are not particularly limited to, compounds 7 to 13 described below and salts thereof. Each of compounds 7 to 11 is preferably in a free form, and each of compounds 12 and 13 is preferably trifluoroacetate.

TABLE 2

| Compound | IUPAC name | Structural formula | Salt | MS |
|---|---|---|---|---|
| 7 | 8-(2,4-Difluorophenoxy)-1-methyl-4,5-dihydro-1H-thieno[3,4-g]indazole-6-carboxamide | 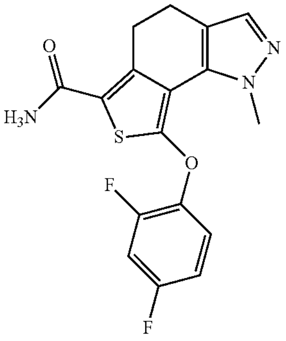 [SMILES: Cn1ncc2c1-c1c(Oc3ccc(F)cc3F)sc(C(N)=O)c1CC2] | | |

TABLE 2-continued
| Compound | IUPAC name | Structural formula | Salt | MS |
|---|---|---|---|---|
| 8 | 4-((4-Fluorophenyl)sulfonyl)-3-(2-(imidazo[1,2-b]pyridazin-6-ylsulfanyl)ethyl)-3,4-dihydroquinoxalin-2(1H)-one | 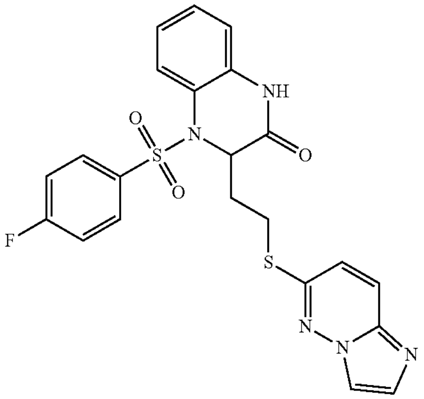 [SMILES: O=C1Nc2ccccc2N(S(=O)(=O)c2ccc(F)cc2)C1CCSc1ccc2nccn2n1] | | |
| 9 | 2-(Benzylamino)-4-(1H-pyrrolo[2,3-b]pyridine-3-yl)benzamide | 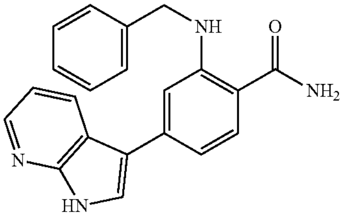 [SMILES: NC(=O)c1ccc(-c2c[nH]c3ncccc23)cc1NCc1ccccc1] | | 343.2 |
| 10 | 3-(3-(Benzyloxy)phenyl)-1H-pyrrolo[2,3-b]pyridine | 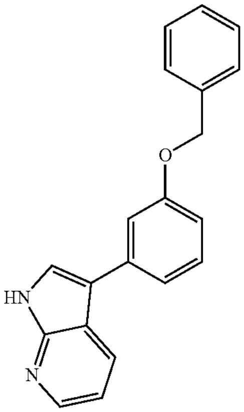 [SMILES: c1ccc(COc2cccc(-c3c[nH]c4ncccc34)c2)cc1] | | |
| 11 | 4-(4-(2,3-Dihydro-1,4-benzodioxin-6-yl)-1H-pyrazol-3-yl)benzene-1,3-diol | 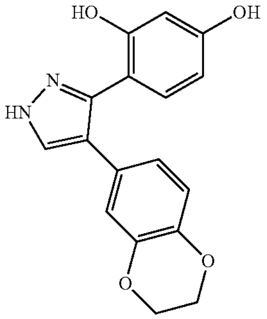 [SMILES: Oc1ccc(-c2n[nH]cc2-c2ccc3c(c2)OCCO3)c(O)c1] | | |

TABLE 2-continued

| Compound | IUPAC name | Structural formula | Salt | MS |
|---|---|---|---|---|
| 12 | N-Butyl-8-(4-methoxyphenyl)-1,6-naphthyridine-2-carboxamide | 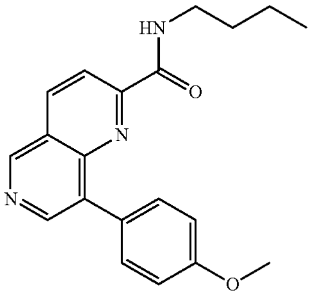 [SMILES: CCCCNC(=O)c1ccc2cncc(-c3ccc(OC)cc3)c2n1] | $CF_3COOH$ | |
| 13 | 8-(4-Methylphenyl)-N,N-dipropyl-1,6-naphthyridine-2-carboxamide | 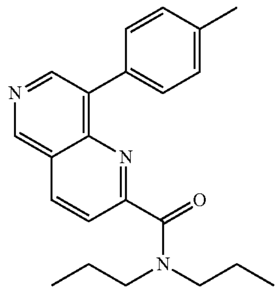 [SMILES: CCCN(CCC)C(=O)c1ccc2cncc(-c3ccc(C)cc3)c2n1] | $CF_3COOH$ | |

The CDK8/19 inhibitor according to the present invention is not limited to the compounds described above, and an antisense oligonucleotide or siRNA against CDK8/19 mRNA, an antibody binding to CDK8/19, a dominant negative CDK8/19 mutant, or the like can also be used as the CDK8/19 inhibitor.

The CDK8/19 inhibitor described above is commercially available or can be synthesized for use according to a known method.

"Insulin-positive cell population" according to the present invention means a cell population comprising insulin-positive cells obtained by the induction of differentiation from pluripotent stem cells. "Insulin-positive cells" means cells characterized in that the expression of a marker of insulin is found. "Insulin-positive cells" are cells that may express a marker of NK6 homeobox 1 (NKX6.1) and preferably express both markers of insulin and NKX6.1 (that is, insulin-positive and NKX6.1-positive cells).

"Insulin-positive cell population" according to the present invention is a cell population enriched in insulin-positive cells, particularly, insulin-positive and NKX6.1-positive cells, as compared with an insulin-positive cell population obtained by the induction of differentiation from pluripotent stem cells according to a conventionally known approach (that is, an approach comprising the step of culturing a pancreatic progenitor cell population or a cell population at a later stage of differentiation in the presence of an ALK5 inhibitor (for example, ALK5 inhibitor II) (Nature Biotechnology 2014; 32: 1121-1133, etc.)). The content percentage of the insulin-positive and NKX6.1-positive cells in the insulin-positive cell population of the present invention is 33% or more, preferably 34% or more, more preferably 35% or more, further preferably 36% or more, especially preferably 37% or more. The upper limit of the content percentage is not particularly limited and is 70% or less, 60% or less, or 50% or less. The content percentage can be expressed using two numeric values respectively selected from the numeric values of the upper limit and the lower limit. The content percentage is, for example, 33% to 50%, preferably 34% to 50%, more preferably 35% to 50%, further preferably 36% to 50%, especially preferably 37% to 50%.

"Insulin-positive cell population" according to the present invention can be obtained by treating a pancreatic progenitor cell population obtained by the induction of differentiation from pluripotent stem cells, or a cell population at a later stage of differentiation with a CDK8/19 inhibitor. The treatment of a cell population at a predetermined stage of differentiation, that is, a pancreatic progenitor cell population or a cell population at a later stage of differentiation, with a CDK8/19 inhibitor can produce an insulin-positive cell population enriched in insulin-positive cells, preferably insulin-positive and NKX6.1-positive cells. The insulin-positive cell population may include other cells (for example, endocrine progenitor cells; other pancreatic hormone-producing cells expressing at least one of the markers glucagon, somatostatin, and pancreatic polypeptide; Ki67-positive cells and CHGA-negative cells), in addition to the insulin-positive cells.

In the present invention, "pancreatic progenitor cell population or cell population at a later stage of differentiation" means a pancreatic progenitor cell population or an endocrine progenitor cell population or means both a pancreatic progenitor cell population and an endocrine progenitor cell population.

As used herein, "pluripotency" means the ability to differentiate into tissues and cells having various different shapes and functions and to differentiate into cells of any lineage of the 3 germ layers. "Pluripotency" is different from "totipotency", which is the ability to differentiate into any tissue of the living body, including the placenta, in that pluripotent cells cannot differentiate into the placenta and therefore, do not have the ability to form an individual.

As used herein, "multipotency" means the ability to differentiate into plural and limited numbers of linages of cells. For example, mesenchymal stem cells, hematopoietic stem cells, neural stem cells are multipotent, but not pluripotent.

As used herein, "pluripotent stem cells" refers to embryonic-stem cells (ES cells) and cells potentially having a pluripotency similar to that of ES cells, that is, the ability to differentiate into various tissues (all of the endodermal, mesodermal, and ectodermal tissues) in the living body. Examples of cells having a pluripotency similar to that of ES cells include "induced pluripotent stem cells" (that may be herein also referred to as "iPS cells"). In the present invention, preferably, pluripotent stem cells are human pluripotent stem cells.

Available "ES cells" include murine ES cells, such as various murine ES cell lines established by inGenious, Institute of Physical and Chemical Research (RIKEN), and the like, and human ES cells, such as various human ES cell lines established by National Institutes of Health (NIH), RIKEN, Kyoto University, Cellartis, and the like. For example, available ES cell lines include CHB-1 to CHB-12, RUES1, RUES2, HUES1 to HUES28 from NIH, and the like; H1 and H9 from WiCell Research Institute; and KhES-1, KhES-2, KhES-3, KhES-4, KhES-5, SSES1, SSES2, SSES3 from RIKEN, and the like.

"Induced pluripotent stem cells" refers to cells that are obtained by reprograming mammalian somatic cells or undifferentiated stem cells by introducing particular factors (nuclear reprogramming factors). At present, there are various "induced pluripotent stem cells" and iPS cells established by Yamanaka, et al. by introducing the 4 factors Oct3/4, Sox2, Klf4, and c-Myc into murine fibroblasts (Takahashi K, Yamanaka S., Cell, (2006) 126: 663-676); iPS cells derived from human cells, established by introducing similar 4 factors into human fibroblasts (Takahashi K, Yamanaka S., et al. Cell, (2007) 131: 861-872.); Nanog-iPS cells established by sorting cells using expression of Nanog as an indicator after introduction of the 4 factors (Okita, K., Ichisaka, T., and Yamanaka, S. (2007). Nature 448, 313-317.); iPS cells produced by a method not using c-Myc (Nakagawa M, Yamanaka S., et al. Nature Biotechnology, (2008) 26, 101-106); and iPS cells established by introducing 6 factors in a virus-free way (Okita K et al. Nat. Methods 2011 May; 8(5): 409-12, Okita K et al. Stem Cells. 31 (3) 458-66) may be also used. Also, induced pluripotent stem cells established by introducing the 4 factors OCT3/4, SOX2, NANOG, and LIN28 by Thomson et al. (Yu J., Thomson JA. et al., Science (2007) 318: 1917-1920.); induced pluripotent stem cells produced by Daley et al. (Park IH, Daley GQ. et al., Nature (2007) 451: 141-146); induced pluripotent stem cells produced by Sakurada et al. (Japanese Unexamined Patent Application Publication No. 2008-307007) and the like may be used.

In addition, any of known induced pluripotent stem cells known in the art described in all published articles (for example, Shi Y., Ding S., et al., Cell Stem Cell, (2008) Vol 3, Issue 5, 568-574; Kim JB., Scholer HR., et al., Nature, (2008) 454, 646-650; Huangfu D., Melton, D A., et al., Nature Biotechnology, (2008) 26, No. 7, 795-797) or patents (for example, Japanese Unexamined Patent Application Publication No. 2008-307007, Japanese Unexamined Patent Application Publication No. 2008-283972, U52008-2336610, U52009-047263, WO2007-069666, WO2008-118220, WO2008-124133, WO2008-151058, WO2009-006930, WO2009-006997, WO2009-007852) may be used.

Available induced pluripotent cell lines include various iPS cell lines established by NIH, Institute of Physical and Chemical Research (RIKEN), Kyoto University and the like. For example, such human iPS cell lines include the RIKEN cell lines HiPS-RIKEN-1A, HIPS-RIKEN-2A, HiPS-RIKEN-12A, and Nips-B2 and the Kyoto University cell lines Ff-WJ-18, Ff-I01s01, Ff-I01s02, Ff-I01s04, Ff-I01s06, Ff-I14s03, Ff-I14s04, QHJI01s01, QHJI01s04, QHJI14s03, QHJI14s04, 253G1, 201B7, 409B2, 454E2, 606A1, 610B1, 648A1, CDI cell lines MyCell iPS Cells (21525.102.10A), MyCell iPS Cells (21526.101.10A), and the like.

As used herein, "pancreatic progenitor cell population" means a cell population comprising pancreatic progenitor cells. As used herein, pancreatic progenitor cells are characterized by the expression of the marker NKX6.1 (that is, the cells are NKX6.1-positive). The pancreatic progenitor cells may further express at least one of the markers PDX-1, PTF-1α, GATA4 and SOX9. Preferably, the pancreatic progenitor cells are characterized by the expression of NKX6.1 and PDX-1 (that is, the cells are NKX6.1-positive and PDX-1-positive).

In one embodiment, "pancreatic progenitor cell population" according to the present invention is a cell population that corresponds to a culture after the completion of step 4) or a culture in step 5) in the process of inducing the differentiation of pluripotent stem cells into pancreatic β cells as described below in detail.

"Pancreatic progenitor cell population" according to the present invention comprises pancreatic progenitor cells at a proportion of 30% or more, preferably 40% or more, more preferably 50% or more, further preferably 60% or more, still further preferably 70% or more. The pancreatic progenitor cell population may include other cells (for example, endocrine progenitor cells, insulin-positive cells, Ki67-positive cells, and CHGA-negative cells), in addition to the pancreatic progenitor cells.

The proportion of specific cells in a cell population described herein can be determined on the basis of a known approach capable of calculating the number of cells, such as flow cytometry.

As used herein, "endocrine progenitor cell population" means a cell population comprising endocrine progenitor cells. As used herein, endocrine progenitor cells mean cells characterized by the expression of at least one of the markers CHGA, NeuroD and NGN3 and no expression of a marker of the pancreas-related hormone system (for example, insulin). The endocrine progenitor cells may express a marker such as PAX-4, NKX2.2, Islet-1, or PDX-1.

In one embodiment, "endocrine progenitor cell population" according to the present invention is a cell population that corresponds to a culture after the completion of step 5) or a culture in step 6) in the process of inducing the differentiation of pluripotent stem cells into pancreatic β cells as described below in detail.

"Endocrine progenitor cell population" according to the present invention comprises endocrine progenitor cells at a proportion of 30% or more, preferably 40% or more, more preferably 50% or more, further preferably 60% or more, still further preferably 70% or more. The endocrine progenitor cell population may include other cells (for example, pancreatic progenitor cells, insulin-positive cells, Ki67-positive cells, and CHGA-negative cells), in addition to the endocrine progenitor cells.

It is known that cells having different features depending on the stages of differentiation appear in the process of differentiation of pluripotent stem cells into insulin-positive cells (WO2009/012428 and WO2016/021734). For example, the stages of differentiation can be broadly classified into pluripotent stem cells, definitive endoderm cells, primitive gut tube cells, posterior foregut cells, pancreatic progenitor cells, endocrine progenitor cells, and insulin-positive cells in order from relatively undifferentiated to differentiated forms.

The pancreatic progenitor cell population or the cell population at a later stage of differentiation can be obtained by use of a known approach of inducing the differentiation of pluripotent stem cells into insulin-positive cells. Specifically, each cell population at a stage of differentiation of interest can be obtained using the following steps of induction of differentiation:

step 1) inducing the differentiation of pluripotent stem cells into definitive endoderm cells;

step 2) inducing the differentiation of the definitive endoderm cells into primitive gut tube cells;

step 3) inducing the differentiation of the primitive gut tube cells into posterior foregut cells;

step 4) inducing the differentiation of the posterior foregut cells into pancreatic progenitor cells;

step 5) inducing the differentiation of the pancreatic progenitor cells into endocrine progenitor cells; and step 6) inducing the differentiation of the endocrine progenitor cells into insulin-positive cells.

Hereinafter, each step will be described, though the induction of differentiation into each cell is not limited by these approaches.

Step 1) Differentiation into Definitive Endoderm Cells

The pluripotent stem cells are first allowed to differentiate into definitive endoderm cells. Methods for inducing the definitive endoderm from pluripotent stem cells have already been known, and any of the methods may be used. Preferably, the pluripotent stem cells are cultured in a medium containing activin A, more preferably a medium containing activin A, a ROCK inhibitor, and a GSK3β inhibitor, to thereby differentiate into definitive endoderm cells. The number of cells at the start of culture is not particularly limited and is 22000 to 150000 cells/cm$^2$, preferably 22000 to 100000 cells/cm$^2$, more preferably 22000 to 80000 cells/cm$^2$. The culture period is 1 day to 4 days, preferably 1 day to 3 days, particularly preferably 3 days.

The culture temperature is not particularly limited, and the culture is performed at 30 to 40° C. (for example, 37° C.). The concentration of carbon dioxide in a culture container is on the order of, for example, 5%. The culture may be performed by any of two-dimensional culture and three-dimensional culture.

The medium used in this step may be a basal medium for use in the culture of mammalian cells, such as RPMI 1640 medium, MEM medium, iMEM medium, DMEM/F12 medium, Improved MEM Zinc Option medium, Improved MEM/1% B-27/Penicillin Streptomycin medium, or MCDB131/20 mM Glucose/$NaHCO_3$/FAF-BSA/ITS-X/GlutaMAX™/ascorbic acid/Penicillin Streptomycin medium.

The concentration of the activin A in the medium is usually 30 to 200 ng/mL, preferably 50 to 150 ng/mL, more preferably 70 to 120 ng/mL, particularly preferably about 100 ng/mL.

In another embodiment, the activin A can be contained at a low dose, for example, in an amount of 5 to 100 ng/mL, preferably 5 to 50 ng/mL, more preferably 5 to 10 ng/mL, in the medium.

In a further alternative embodiment, the concentration of the activin A in the medium is about 0.1 to 100 ng/mL, preferably about 1 to 50 ng/mL, more preferably about 3 to 10 ng/mL.

The concentration of the GSK3β inhibitor in the medium is appropriately set depending on the type of the GSK3β inhibitor used. For example, in the case of using CHIR99021 as the GSK3β inhibitor, its concentration is usually 2 to 5 μM, preferably 2 to 4 μM, particularly preferably about 3 μM.

The concentration of the ROCK inhibitor in the medium is appropriately set depending on the type of the ROCK inhibitor used. For example, in the case of using Y27632 as the ROCK inhibitor, its concentration is usually 5 to 20 μM, preferably 5 to 15 μM, particularly preferably about 10 μM.

The medium can be further supplemented with insulin. The insulin can be contained in an amount of 0.01 to 20 μM, preferably 0.1 to 10 μM, more preferably 0.5 to 5 μM, in the medium. The concentration of the insulin in the medium may be, but is not limited to, the concentration of insulin contained in added B-27 supplement.

In a particular embodiment, the cells are cultured for 1 day in a medium containing activin A, a ROCK inhibitor, and a GSK3β inhibitor and then further cultured for 2 days in a medium containing only activin A with the medium replaced with a fresh one every day. Alternatively, the pluripotent stem cells can be subjected to first culture in a medium containing 0.01 to 20 μM insulin in the presence of a low dose of activin A and subsequently subjected to second culture in an insulin-free medium, for production.

Step 2) Differentiation into Primitive Gut Tube Cells

The definitive endoderm cells obtained in step 1) are further cultured in a medium containing a growth factor to induce their differentiation into primitive gut tube cells. The culture period is 2 days to 8 days, preferably about 4 days.

The culture temperature is not particularly limited, and the culture is performed at 30 to 40° C. (for example, 37° C.). The concentration of carbon dioxide in a culture container is on the order of, for example, 5%. The culture may be performed by any of two-dimensional culture and three-dimensional culture.

A basal medium for use in the culture of mammalian cells can be used as culture medium, as in step 1). The medium may be appropriately supplemented with a serum replacement, a vitamin, an antibiotic, and the like, in addition to the growth factor.

The growth factor is preferably EGF, KGF, and/or FGF10, more preferably EGF and/or KGF, further preferably KGF.

The concentration of the growth factor in the medium is appropriately set depending on the type of the growth factor used and is usually about 0.1 nM to 1000 μM, preferably about 0.1 nM to 100 μM. In the case of EGF, its concentration is about 5 to 2000 ng/ml (that is, about 0.8 to 320 nM), preferably about 5 to 1000 ng/ml (that is, about 0.8 to 160 nM), more preferably about 10 to 1000 ng/ml (that is, about 1.6 to 160 nM). In the case of FGF10, its concentration is about 5 to 2000 ng/ml (that is, about 0.3 to 116 nM), preferably about 10 to 1000 ng/ml (that is, about 0.6 to 58 nM). For example, in the case of using KGF as the growth factor, its concentration is usually 5 to 150 ng/mL, preferably 30 to 100 ng/mL, particularly preferably about 50 ng/mL. Step 3) Differentiation into posterior foregut cells The primitive gut tube cells obtained in step 2) are further cultured in a medium containing a growth factor, cyclopamine, noggin, and the like to induce their differentiation into posterior foregut cells. The culture period is 1 day to 5 days, preferably about 2 days. The culture may be performed by any of two-dimensional culture and three-dimensional culture.

The culture temperature is not particularly limited, and the culture is performed at 30 to 40° C. (for example, 37° C.). The concentration of carbon dioxide in a culture container is on the order of, for example, 5%.

As in step 1), a basal medium for use in the culture of mammalian cells can be used as culture medium. The medium may be appropriately supplemented with a serum replacement, a vitamin, an antibiotic, and the like, in addition to the growth factor.

The growth factor is preferably EGF, KGF, and/or FGF10, more preferably EGF and/or KGF, further preferably KGF.

The concentration of the growth factor in the medium is appropriately set depending on the type of the growth factor used and is usually about 0.1 nM to 1000 μM, preferably about 0.1 nM to 100 μM. In the case of EGF, its concentration is about 5 to 2000 ng/ml (that is, about 0.8 to 320 nM), preferably about 5 to 1000 ng/ml (that is, about 0.8 to 160 nM), more preferably about 10 to 1000 ng/ml (that is, about 1.6 to 160 nM). In the case of FGF10, its concentration is about 5 to 2000 ng/ml (that is, about 0.3 to 116 nM), preferably about 10 to 1000 ng/ml (that is, about 0.6 to 58 nM). For example, in the case of using KGF as the growth factor, its concentration is usually 5 to 150 ng/mL, preferably 30 to 100 ng/mL, particularly preferably about 50 ng/mL.

The concentration of the cyclopamine in the medium is not particularly limited and is usually 0.5 to 1.5 μM, preferably 0.3 to 1.0 μM, particularly preferably about μM.

The concentration of the noggin in the medium is not particularly limited and is usually 10 to 200 ng/mL, preferably 50 to 150 ng/mL, particularly preferably about 100 ng/mL.

Step 4) Differentiation into Pancreatic Progenitor Cells

The posterior foregut cells obtained in step 3) are further cultured in a medium containing a factor having CDK8/19-inhibiting activity, preferably a medium containing a factor having CDK8/19-inhibiting activity and a growth factor, to induce their differentiation into pancreatic progenitor cells. The culture period is 2 days to 10 days, preferably about 5 days. The culture may be performed by any of two-dimensional culture and three-dimensional culture.

In the case of two-dimensional culture, according to the previous report (Toyoda et al., Stem cell Research (2015) 14, 185-197), the posterior foregut cells obtained in step 3) are treated with 0.25% trypsin-EDTA solution and dispersed in the solution by pipetting to obtain a cell dispersion, and the obtained dispersion is subjected to centrifugal separation. Recovered cells are resuspended in a small amount of a fresh medium and the cell suspension is reseeded to a fresh medium of step 4).

As in step 1), a basal medium for use in the culture of mammalian cells can be used as culture medium. The medium may be appropriately supplemented with a serum replacement, a vitamin, an antibiotic, and the like, in addition to the growth factor.

Each of the compounds mentioned above or salts thereof can be used as the factor having CDK8/19-inhibiting activity. The amount of the factor added to the medium is appropriately determined according to the compound or the salt thereof used and is usually about 0.00001 μM to 5 μM, preferably 0.00001 μM to 1 μM. The concentration of the factor having CDK8/19-inhibiting activity in the medium is preferably a concentration that attains inhibitory activity of 50% or more for CDK8/19.

The growth factor is preferably EGF, KGF, and/or FGF10, more preferably KGF and/or EGF, further preferably KGF and EGF.

The concentration of the growth factor in the medium is appropriately set depending on the type of the growth factor used and is usually about 0.1 nM to 1000 μM, preferably about 0.1 nM to 100 μM. In the case of EGF, its concentration is about 5 to 2000 ng/ml (that is, about 0.8 to 320 nM), preferably about 5 to 1000 ng/ml (that is, about 0.8 to 160 nM), more preferably about 10 to 1000 ng/ml (that is, about 1.6 to 160 nM). In the case of FGF10, its concentration is about 5 to 2000 ng/ml (that is, about 0.3 to 116 nM), preferably about 10 to 1000 ng/ml (that is, about 0.6 to 58 nM). For example, in the case of using KGF and EGF as the growth factor, the concentration of EGF is usually 5 to 150 ng/mL, preferably 30 to 100 ng/mL, particularly preferably about ng/mL, and the concentration of KGF is usually 10 to 200 ng/mL, preferably 50 to 150 ng/mL, particularly preferably about 100 ng/mL.

Culture on the first day in step 4) may be performed in the presence of a ROCK inhibitor, and culture on the following days may be performed in a medium containing no ROCK inhibitor.

The medium may also contain a protein kinase C (PKC) activator. PdBU (PKC activator II), TPB (PKC activator V), or the like is used as the PKC activator, though the PKC activator is not limited thereto. The concentration of the PKC activator to be added is about 0.1 to 100 ng/ml, preferably about 1 to 50 ng/ml, more preferably about 3 to 10 ng/ml.

The medium may also be supplemented with dimethyl sulfoxide and/or activin (1 to 50 ng/ml).

In any of the steps, the medium may be supplemented with a serum replacement (for example, B-27 supplement, ITS-G), in addition to the components described above. Also, an amino acid, L-glutamine, GlutaMAX (product name), a non-essential amino acid, a vitamin, nicotinamide, an antibiotic (for example, Antibiotic-Antimycotic, penicillin, streptomycin, or a mixture thereof), an antimicrobial agent (for example, amphotericin B), an antioxidant, pyruvic acid, a buffer, inorganic salts, and the like may be added thereto, if necessary. In the case of adding an antibiotic to the medium, its concentration in the medium is usually 0.01 to 20% by weight, preferably 0.1 to 10% by weight. The culture may be performed by any of two-dimensional culture and three-dimensional culture.

In the case of two-dimensional culture, the cell culture is performed by adherent culture without the use of feeder cells. For the culture, a culture container, for example, a dish, a flask, a microplate, or a cell culture sheet such as OptiCell (product name) (Nunc), is used. The culture container is preferably surface-treated in order to improve adhesiveness to cells (hydrophilicity), or coated with a substrate for cell adhesion such as collagen, gelatin, poly-L-lysine, poly-D-lysine, laminin, fibronectin, Matrigel (for example, BD Matrigel (Nippon Becton Dickinson Company, Ltd.)), or vitronectin. The culture container is preferably a culture container coated with type I-collagen, Matrigel, fibronectin, vitronectin or poly-D-lysine, more preferably a culture container coated with Matrigel or poly-D-lysine.

The culture temperature is not particularly limited, and the culture is performed at 30 to 40° C. (for example, 37° C.). The concentration of carbon dioxide in a culture container is on the order of, for example, 5%.

The pancreatic progenitor cells obtained in step 4) can be further purified using a known surface marker glycoprotein 2 (GP2) or the like. The purification can be performed by a method known per se, for example, using anti-GP2 antibody-immobilized beads.

Step 5) Differentiation into Endocrine Progenitor Cells

The pancreatic progenitor cells obtained in step 4) are further cultured in a medium containing a growth factor to induce their differentiation into endocrine progenitor cells.

The culture may be performed by any of two-dimensional culture and three-dimensional culture. In the case of two-dimensional culture, the pancreatic progenitor cells obtained in step 4) are treated with 0.25% trypsin-EDTA solution and dispersed in the solution by pipetting to obtain a cell dispersion, and the obtained dispersion is subjected to centrifugal separation. Recovered cells are resuspended in a small amount of a fresh medium and the cell suspension is reseeded to a fresh medium of step 5). The culture period is 2 days to 3 days, preferably about 2 days.

As in step 1), a basal medium for use in the culture of mammalian cells can be used as culture medium. The medium is supplemented with SANT1, retinoic acid, ALK5 inhibitor II, T3, and LDN according to the previous report (Nature Biotechnology 2014; 32: 1121-1133) and may be appropriately further supplemented with a Wnt inhibitor, a ROCK inhibitor, FGF (preferably FGF2), a serum replacement, a vitamin, an antibiotic, and the like. In the present invention, in the case of using a CDK8/19 inhibitor in step 5), an ALK5 inhibitor (ALK5 inhibitor II, etc.) may not be used. Preferably, an ALK5 inhibitor (ALK5 inhibitor II, etc.) is not used.

The culture is performed by nonadherent culture without the use of feeder cells. For the culture, a dish, a flask, a microplate, a porous plate (Nunc), or the like, or a bioreactor is used. The culture container is preferably surface-treated in order to decrease adhesiveness to cells.

The culture temperature is not particularly limited, and the culture is performed at 30 to 40° C. (for example, 37° C.). The concentration of carbon dioxide in a culture container is on the order of, for example, 5%.

The endocrine progenitor cells obtained in step 5) can be further purified using a known surface marker glycoprotein 2 (GP2) or the like. The purification can be performed by a method known per se, for example, using anti-GP2 antibody-immobilized beads.

Step 6) Differentiation into Insulin-Positive Cells

The endocrine progenitor cells obtained in step 5) are further cultured in a medium containing a growth factor to induce their differentiation into insulin-positive cells. The culture period is 10 days to 30 days, preferably about 10 to 20 days.

As in step 1), a basal medium for use in the culture of mammalian cells can be used as culture medium. The medium is supplemented with ALK5 inhibitor II, T3, LDN, γ-secretase inhibitor XX, γ-secretase inhibitor RO, N-cysteine, an AXL inhibitor, and ascorbic acid according to the previous report (Nature Biotechnology 2014; 32: 1121-1133) and may be appropriately further supplemented with a Wnt inhibitor, a ROCK inhibitor, FGF (preferably FGF2), a serum replacement, a vitamin, an antibiotic, and the like. For example, the medium may be supplemented with ALK5 inhibitor II, T3, LDN, γ-secretase inhibitor RO, and ascorbic acid or may be supplemented with T3, ALK5 inhibitor II, $ZnSO_4$, heparin, N-acetylcysteine, Trolox, and R428. In the present invention, in the case of using a CDK8/19 inhibitor in step 6), an ALK5 inhibitor (ALK5 inhibitor II, etc.) may not be used. Preferably, an ALK5 inhibitor (ALK5 inhibitor II, etc.) is not used.

The culture may be performed by any of two-dimensional culture and three-dimensional culture. The culture does not employ feeder cells. Three-dimensional culture is performed by nonadherent culture. For the culture, a dish, a flask, a microplate, a porous plate (Nunc), or the like, or a bioreactor is used. The culture container is preferably surface-treated in order to decrease adhesiveness to cells.

The culture temperature is not particularly limited, and the culture is performed at 30 to 40° C. (for example, 37° C.). The concentration of carbon dioxide in a culture container is on the order of, for example, 5%.

The pancreatic progenitor cell population obtained by the induction of differentiation from pluripotent stem cells, or the cell population at a later stage of differentiation can be treated with the CDK8/19 inhibitor by the contact of the cell population with the CDK8/19 inhibitor. For example, the treatment can be performed by culturing the cell population in a medium supplemented with the CDK8/19 inhibitor. The CDK8/19 inhibitor can be contained in any amount capable of inhibiting CDK8/19 activity in the medium, and can be contained in an amount of, for example, 10 μM or less, 5 μM or less, 4 μM or less, 3 μM or less, 2 μM or less, or 1 μM or less. Particularly, when the CDK8/19 inhibitor has inhibitory activity for ALK5 and its concentration necessary for exhibiting an inhibition rate of 50% (IC H value) against ALK5 is 1 μM or more, the CDK8/19 inhibitor can be contained in an amount of less than 1 μM. The lower limit of the amount of the CDK8/19 inhibitor added is not particularly limited and can be 0.1 μM or more, 0.2 μM or more, 0.3 μM or more, 0.4 μM or more, or 0.5 μM or more. The amount of the CDK8/19 inhibitor added is, for example, 10 μM or less and 0.1 μM or more, preferably 5 μM or less and 0.1 μM or more, more preferably 1 μM or less and 0.1 μM or more, for example, less than 1 μM and 0.1 μM or more.

The culture of the pancreatic progenitor cell population obtained by the induction of differentiation from pluripotent stem cells, or the cell population at a later stage of differentiation in the presence of the CDK8/19 inhibitor can be performed for at least 12 hours, preferably 24 hours or longer, 2 days or longer, 4 days or longer, 8 days or longer, 10 days or longer, or 15 days or longer. The culture in the presence of the CDK8/19 inhibitor is preferably performed for 4 days or longer. The medium may be replaced during the period of treatment with the CDK8/19 inhibitor and can be replaced with a medium supplemented with the CDK8/19 inhibitor, having the same or different composition as or from that before the replacement, according to the culture schedule.

The pancreatic progenitor cell population obtained by the induction of differentiation from pluripotent stem cells, or the cell population at a later stage of differentiation can be subjected to the step of further differentiation into the cell population of interest, in addition to being treated with the CDK8/19 inhibitor. As used herein, "in addition to being treated with the CDK8/19 inhibitor" includes the case of performing the step of treatment with the CDK8/19 inhibitor and the step of differentiation at the same time, the case of treating the cell population with the CDK8/19 inhibitor, followed by the step of differentiation, and the case of subjecting the cell population to the step of differentiation, followed by the step of treatment with the CDK8/19 inhibitor. Thus, the medium for use in the treatment with the CDK8/19 inhibitor and the medium for use in the differentiation of the cell population may be separate media, or the medium for use in the step of differentiation may be further supplemented with the CDK8/19 inhibitor.

In one embodiment of the present invention, the CDK8/19 inhibitor is contained in a medium in step 5 or later, that is, a medium in step 5 or a medium in step 6, or a medium in step 5 and a medium in step 6, and allowed to act on the cells, in the process of inducing the differentiation of pluripotent stem cells into insulin-positive cells.

The differentiation of the insulin-positive cell population obtained by the present invention into a cell population comprising pancreatic β cells (hereinafter, referred to as "pancreatic β cell population") can be induced. As used herein, "pancreatic β cells" means cells more mature than "insulin-positive cells" and specifically means cells characterized by expressing at least one of the markers MAFA, UCN3, and IAPP, which are maturation markers of pancreatic β cells, or by a reaction to increase insulin secretion by glucose stimulation. The pancreatic β cell population may include other cells (for example, insulin-positive cells, Ki67-positive cells and CHGA-negative cells), in addition to the pancreatic β cells.

The pancreatic β cell population can be obtained by the differentiation and/or maturation, preferably the in vivo differentiation and/or maturation in an animal, of the insulin-positive cell population.

"Animal" is preferably a mammal. Examples thereof include humans, nonhuman primates, pigs, cattle, horses, sheep, goats, llamas, dogs, cats, rabbits, mice, and guinea pigs. A human is preferred.

The transplantation is preferably performed to an in vivo region where the cell population can be fixed at a given position, and can be performed, for example, subcutaneously, intraperitoneally, to the peritoneal mesothelium, to the greater omentum, to a fat tissue, to a muscle tissue, or beneath the capsule of each organ such as the pancreas or the kidney, in the animal. The number of cells to be transplanted may vary depending on factors such as the stage of differentiation of the cells to be transplanted, the age and body weight of a recipient, the size of a transplantation site, and the severity of a disease and is not particularly limited. For example, the number of cells can be on the order of $10\times10^4$ cells to $10\times10^{11}$ cells. The transplanted cell population is induced to differentiate in an in vivo environment and can thereby differentiate into the cell population of interest, preferably a pancreatic β cell population, which may then be recovered or may be indwelled in vivo as it is.

For the transplantation, the cell population may be embedded in a gel containing a biocompatible material and then transplanted. For example, the cell population embedded in the gel containing a biocompatible material may be enclosed in a device such as a capsule, a bag, or a chamber and transplanted into a living body.

As used herein, "embedding" means that an endocrine progenitor cell population or a cell population at a later stage of differentiation is contained in a scattered manner in the gel containing a biocompatible material.

As used herein, "biocompatible material" means an arbitrary material that induces neither marked immune response nor harmful biological reaction (for example, toxic reaction and blood coagulation) when transplanted into a living body and indwelled for a short period or a long period. Also, "biocompatible material" is preferably a biodegradable material. Examples of such a material include polylactic acid (PLA), polycaprolactone (PCL), polyurethane (PU), polyethylene glycol (PEG), polyhydroxyethyl methacrylate, polyglycolic acid (PGA), poly(lactic-co-glycolic acid) (PLGA), poly(3-hydroxybutyrate-co-hydroxyvalerate) (PHBV), poly(ethylene-co-vinyl acetate) (PEVA)polyacrylamide, polyethylene oxide, polyethyleneamine, polyhydroxybutyric acid, poly(N-vinylpyrrolidone), polyvinyl alcohol, polypropylene fumarate, polyacrylic acid, poly-e-caprolactone, polymethacrylic acid, polyvinylidene difluoride (PVDF), pectic acid, hyaluronic acid, heparin sulfate, chondroitin sulfate, heparan sulfate proteoglycan, heparin, chitin, chitosan, xanthan, carboxymethylcellulose, carboxymethyl chitosan, alginate, alginic acid ester, collagen, cellulose, silk fibroin, keratin, gelatin, fibrin, pullulan, laminin, gellan, silicon, urethane, elastin and modified forms thereof, and combinations thereof. The surface of "biocompatible material" may be modified (for example, coated with a substrate for cell adhesion (collagen, gelatin, poly-L-lysine, poly-D-lysine, laminin, fibronectin, Matrigel, vitronectin, etc.)) so as to permit cell adhesion or may be engineered with a functional group (for example, an amino group, a carboxyl group, a hydroxy group, a methacrylic acid group, and an acrylic acid group) known to control cell proliferation, differentiation, or functions, if necessary. In a particular embodiment, alginate or alginic acid ester can be suitably used as "biocompatible material".

The alginate can be a water-soluble salt, and a metal salt, an ammonium salt, or the like can be used. For example, sodium alginate, calcium alginate, or ammonium alginate can be suitably used.

The alginic acid ester (also referred to as propylene glycol alginate) is a derivative in which propylene glycol is bonded to the carboxyl group of alginic acid through an ester bond.

The ratio of mannuronic acid to guluronic acid (M/G ratio) contained in the alginate is arbitrary. In general, in the case of M>G, a highly flexible gel can be formed. In the case of M<G, a strong gel can be formed. In the present invention, alginate containing guluronic acid at a proportion of 10 to 90%, 20 to 80%, 30 to 70%, or 40 to 60% can be used.

The gel can be prepared using alginate or alginic acid ester in accordance with a known approach (WO2010/032242 and WO2011/154941) and can be obtained by adding a cross-linking agent to a solution of alginate or alginic acid ester for gelation.

The alginate or the alginic acid ester can be contained in an amount of 0.05 to 10% by weight, preferably 0.1 to 5% by weight, more preferably 0.5 to 3% by weight, in a solvent. The solvent can be any solvent capable of dissolving the alginate or the alginic acid ester, and water, physiological saline, or the like can be used.

The cross-linking agent can be any cross-linking agent that can allow a solution of alginate or alginic acid ester to gelate, and is not particularly limited. A polyvalent metal cation can be used. The polyvalent metal cation is preferably a divalent metal cation, more preferably a calcium ion, a strontium ion, or a barium ion. The cross-linking agent can be used in the form of a salt. In the present invention, at least one member selected from calcium chloride, strontium chloride, and barium chloride can be used as the cross-linking agent.

The gel containing alginate or alginic acid ester can contain a nanofiber. The nanofiber is a natural or synthetic fiber having a diameter of a nanometer order. Examples of the natural nanofiber include nanofibers containing one or more of collagen, cellulose, silk fibroin, keratin, gelatin, and polysaccharides such as chitosan. Examples of the synthetic nanofiber include polylactic acid (PLA), polycaprolactone (PCL), polyurethane (PU), poly(lactide-co-glycolide) (PLGA), poly(3-hydroxybutyrate-co-hydroxyvalerate) (PHBV), and poly(ethylene-co-vinylacetate) (PEVA). The nanofiber can be contained in an amount of less than 1% by weight, for example, 0.9% by weight, 0.8% by weight, 0.7% by weight, 0.6% by weight, 0.5% by weight, or less than the amount, in the gel containing alginic acid. The lower limit of the amount of the nanofiber contained in the gel containing alginate or alginic acid ester is not particularly limited and can be 0.05% by weight or more, preferably 0.1% by weight or more.

The embedding of the cell population in the gel containing alginate or alginic acid ester can be performed by an arbitrary approach and can be performed, for example, by mixing the cell population into a solution of alginate or alginic acid ester and gelating it, though the embedding is not particularly limited thereto.

The cell population can be contained in an amount selected from $1\times10^4$ cells to $1\times10^9$ cells/mL, preferably $1\times10^7$ cells to $1\times10^8$ cells/mL, in the solution of alginate or alginic acid ester.

The gelation of the solution of alginate or alginic acid ester containing the cell population can be performed by adding a cross-linking agent to the solution. The amount of the cross-linking agent added can be an amount selected from 0.1 to 5% by weight, for example, 0.1 to 1% by weight, with respect to the solution. The gelation can be performed in a container having a predetermined configuration and/or shape for use in cell culture or cell transplantation, or in a mold designed so as to obtain a gel adapted to the container.

Alternatively, the gelation may be performed by forming a gel capsule containing alginic acid in accordance with a known approach (WO2010/010902). Specifically, the solution of alginate or alginic acid ester containing the cell population may be added dropwise to a solution of a cross-linking agent for gelation. The size of liquid droplets can be adjusted according to the shape of a nozzle for dropwise addition or a dropwise addition method, and by extension, the size of the gel capsule containing alginic acid can be defined. The dropwise addition method is not particularly limited and can be performed by an approach such as an air spray method, an airless spray method, or a static spray method. The size of the gel capsule containing alginic acid is not particularly limited and can be a diameter of 5 mm or smaller, 1 mm or smaller, or 500 μm or smaller. The cross-linking agent solution can contain the cross-linking agent in an amount selected from 0.1 to 10% by weight, for example, 0.1 to 5% by weight.

The insulin-positive cell population obtained by the present invention may be indwelled as it is and used as insulin-producing and/or -secreting cells, when transplanted into a living body of an animal and differentiated in the living body of the animal.

The insulin-positive cell population obtained by the present invention is transplanted as it is or in a capsule form to an affected area and is thereby useful as a cell medicine for treating diabetes mellitus, particularly, type I diabetes mellitus.

The insulin-positive cell population obtained by the present invention may be a prodrug. As used herein, the prodrug refers to a cell population that is differentiated after transplantation into a living body and converted to cells having a function of treating a disease.

The insulin-positive cell population obtained by the present invention has low toxicity (for example, acute toxicity, chronic toxicity, genetic toxicity, reproductive toxicity, cardiotoxicity, and carcinogenicity) and can be safely administered as it is or in the form of a pharmaceutical composition containing the cell population mixed with a pharmacologically acceptable carrier, etc. to a mammal (for example, a mouse, a rat, a hamster, a rabbit, a cat, a dog, cattle, sheep, a monkey, and a human).

3. Differentiation Medium

The present invention provides a differentiation medium for a pancreatic progenitor cell population or a cell population at a later stage of differentiation, comprising a CDK8/19 inhibitor.

The differentiation medium of the present invention can be used to induce differentiation of a pancreatic progenitor cell population or a cell population at a later stage of differentiation. The differentiation medium of the present invention can be used in step 5) or step 6) in the aforementioned method for inducing the differentiation of pluripotent stem cells into insulin-positive cells.

The differentiation medium of the present invention comprises the CDK8/19 inhibitor in any amount capable of inhibiting CDK8/19 activity in a basal medium for use in the culture of mammalian cells, such as RPMI 1640 medium, MEM medium, iMEM medium, DMEM/F12 medium, Improved MEM Zinc Option medium, Improved MEM/1% B-27/Penicillin Streptomycin medium, or MCDB131/20 mM Glucose/$NaHCO_3$/FAF-BSA/ITS-X/GlutaMAX™/Ascorbic acid/Penicillin Streptomycin medium. The amount of the CDK8/19 inhibitor contained in the medium is as defined above.

The differentiation medium of the present invention further contains other factors required for each of step 5) and step 6), such as a growth factor, various inhibitors, a serum replacement, an antibiotic, and a vitamin, in addition to the CDK8/19 inhibitor. According to the previous report (Nature Biotechnology 2014; 32: 1121-1133), for example, the medium for use in step 5) can be supplemented with predetermined amounts of SANT1, retinoic acid, T3, LDN, a Wnt inhibitor, a ROCK inhibitor, FGF (preferably FGF2), a serum replacement, a vitamin, an antibiotic, and the like. The medium for use in step 6) can be supplemented with predetermined amounts of T3, LDN, γ-secretase inhibitor XX, γ-secretase inhibitor RO, N-cysteine, an AXL inhibitor, ascorbic acid, a Wnt inhibitor, a ROCK inhibitor, FGF (preferably FGF2), a serum replacement, a vitamin, an antibiotic, $ZnSO_4$, heparin, N-acetylcysteine, Trolox, R428, and the like.

The differentiation medium of the present invention has substantially no ALK5-inhibiting activity. "Have substantially no ALK5-inhibiting activity" not only means that the medium has no ALK5-inhibiting activity but includes the case where the inhibition rate against ALK5 is less than 50%, preferably 40% or less, more preferably 30% or less, further preferably 20% or less, still further preferably 10% or less, especially preferably 5% or less, as defined above. The differentiation medium of the present invention may contain a compound having ALK5-inhibiting activity (for example, ALK5 inhibitor II) as long as the definition is satisfied.

The differentiation medium of the present invention may be provided in one form of a mixture of a basal medium, the CDK8/19 inhibitor and other factors described above, or may be provided in any combination or in a plurality of separate forms of these components and prepared just before use.

Hereinafter, the present invention will be described with reference to Examples. However, the present invention is not limited by these Examples.

EXAMPLES

Example 1: Evaluation of ALK4-Inhibiting Activity, ALK5-Inhibiting Activity, CDK8-Inhibiting Activity and CDK19-Inhibiting Activity The test compounds diethyl (E)-(4-(3-(5-(4-fluorophenyl)-1-methyl-1H-pyrazol-4-yl)acrylamido)benzyl)phosphonate (compound 1), 2-(4-(4-(isoquinolin-4-yl)phenyl)-

1H-pyrazol-1-yl)-N,N-dimethylacetamide (compound 2 (BI-1347)), and 4-((2-(6-(4-methylpiperazine-1-carbonyl) naphthalen-2-yl)ethyl)amino)quinazoline-6-carbonitrile (compound 3 (Senexin B)) were evaluated for their ALK4-inhibiting activity, ALK5-inhibiting activity, CDK8-inhibiting activity and CDK19-inhibiting activity by the following method.

In the kinase panel test, 0.1 μM or 1 μM (that is, the seventh or sixth power of the $-Log_{10}$ value) of each test compound was added to each of the kinases ALK4, ALK5, CDK8, and CDK19, and binding-inhibiting activity thereof was measured from 0 to 100%. Estimate $pIC_{50}$ was calculated from the obtained two values and indicated by a value of 6 to 8. In the table, $pIC_{50}$=6 means that no binding-inhibiting activity was exhibited at any of the addition concentrations 0.1 μM and 1 μM in this measurement test, suggesting that the compound has no inhibitory activity or has only weak binding-inhibiting activity with $pIC_{50}\leq6$. Likewise, $pIC_{50}$=8 means that the estimate $pIC_{50}$ value determined from the binding-inhibiting activity at 0.1 μM and 1 μM was 8 or more and strong binding activity with $pIC_{50}\geq8$ was exhibited.

Table 3 shows the concentrations of each test compound necessary for exhibiting an inhibition rate of 50% (estimate $pIC_{50}$ values) against ALK4, ALK5, CDK8, and CDK19.

TABLE 3

| | ALK4 | ALK5 | CDK8 | CDK19 |
|---|---|---|---|---|
| Compound 1 | | | | |
| Estimate $pIC_{50}$ value | 6 | 6 | 7.27 | 7.76 |
| Compound 2 | | | | |
| Estimate $pIC_{50}$ value | 6 | 6 | 8 | 8 |
| Compound 3 | | | | |
| Estimate $pIC_{50}$ value | 6 | 6 | 7.89 | 8 |

In the table, as for the estimate $pIC_{50}$ value, "6" depicts $IC_{50}\geq$ 1 μM, and "8" depicts $IC_{50}\leq$ 10 nM.

From Table 3, compound 1, compound 2, and compound 3 were confirmed to strongly inhibit CDK8 and CDK19.

Example 2: Increase in the proportion of cells of interest (insulin-positive and NKX6.1-positive cells) in cell population obtained by treating pancreatic progenitor cell population with CDK8/19 inhibitor 1. Method The induction of differentiation of iPS cells into a pancreatic progenitor cell population was carried out according to the above steps 1)-4), the previous report (Stem Cell Research (2015) 14, 185-197), etc. The induction of differentiation into insulin-positive cells was carried out according to the above step 5), 6), etc.

The pancreatic progenitor cell population obtained by the induction of differentiation from iPS cells was cultured for 2 days in a medium for induction of differentiation (Improved MEM/1% B27/Penicillin Streptomycin medium) containing differentiation factors (SANT1, retinoic acid, T3, LDN, a Wnt inhibitor, a ROCK inhibitor, and FGF2) as well as ALK5 inhibitor II (10 μM) or a predetermined concentration of the CDK8/19 inhibitor (compound 1, compound 2 or compound 3) or neither ALK5 inhibitor II nor the CDK8/19 inhibitor and thereby induced to differentiate into an endocrine progenitor cell population.

Subsequently, the endocrine progenitor cell population was cultured for 7 days in a medium for induction of differentiation (Improved MEM/1% B27/Penicillin Streptomycin medium) containing differentiation factors (T3, LDN, γ-secretase inhibitor RO, and FGF receptor 1 inhibitor PD-166866) as well as ALK5 inhibitor II (10 μM) or a predetermined concentration of the CDK8/19 inhibitor (compound 1, compound 2 or compound 3) or neither ALK5 inhibitor II nor the CDK8/19 inhibitor, and then cultured for 4 days in a medium for induction of differentiation (MCDB131/20 mM Glucose/NaHCO3/FAF-BSA/ITS-X/Glutamax/Penicillin Streptomycin medium) containing T3, LDN, γ-secretase inhibitor RO, N-acetylcysteine, AXL inhibitor R428, ascorbic acid, a ROCK inhibitor, $ZnSO_4$, heparin, and Trolox as well as ALK5 inhibitor II (10 μM) or a predetermined concentration of the CDK8/19 inhibitor or neither ALK5 inhibitor II nor the CDK8/19 inhibitor according to the previous report (Nature Biotechnology 2014; 32: 1121-1133) and thereby induced to differentiate into an insulin-positive cell population.

The number of insulin-positive and NKX6.1-positive cells and the number of insulin-positive and NKX6.1-negative cells in the insulin-positive cell population obtained by the above method was counted by flow cytometry to determine the proportion of the cells of interest, that is, the insulin-positive and NKX6.1-positive cells, and the proportion of unintended cells, that is, the insulin-positive and NKX6.1-negative cells, in each cell population.

2. Results

Figure 2:
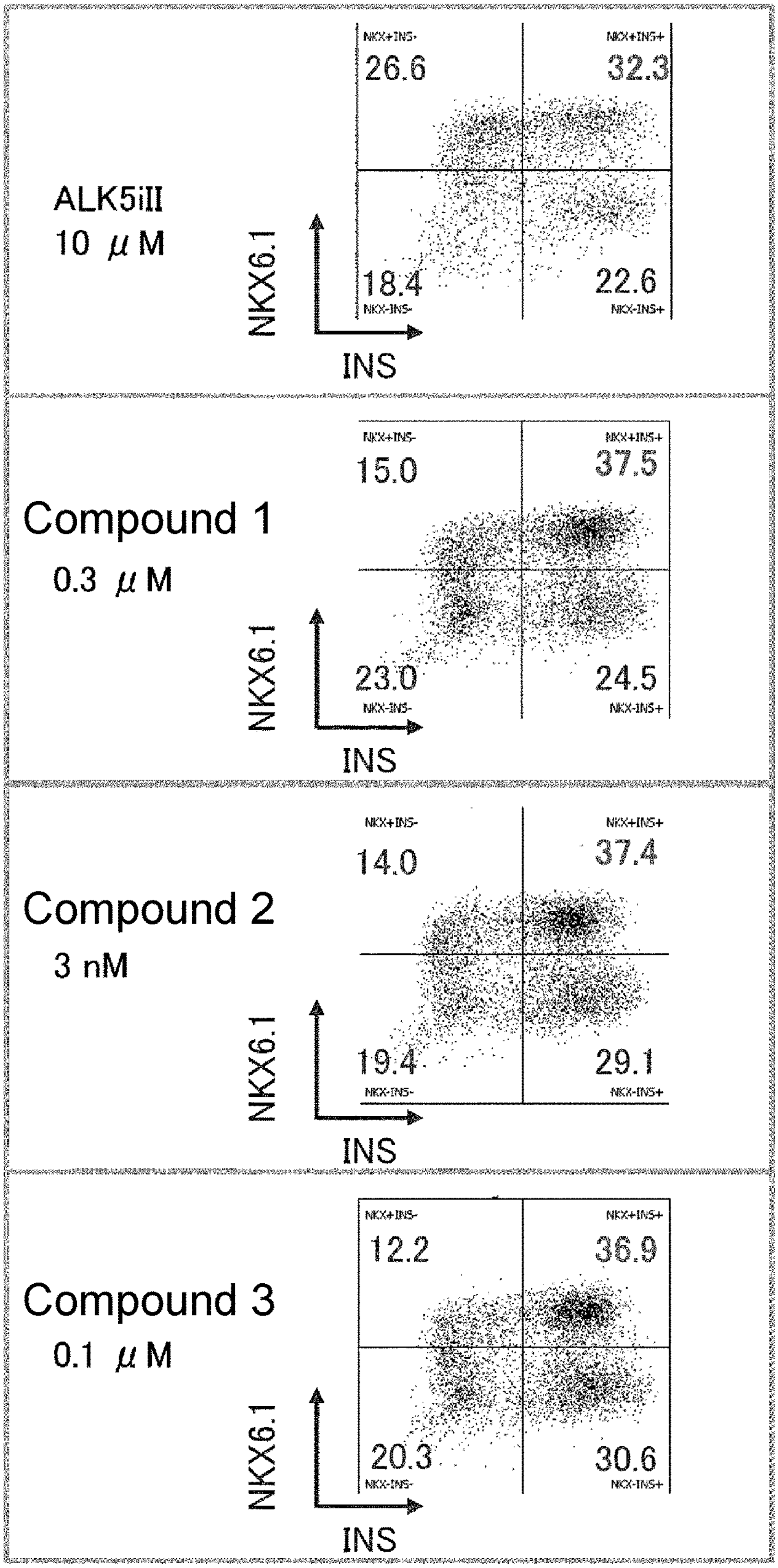
FIG. 2 shows results of expression analysis of insulin and NKX6.1 by flow cytometry of an insulin-positive cell population obtained by treating a pancreatic progenitor cell population with a medium for induction of differentiation containing a predetermined concentration of ALK5 inhibitor II or a CDK8/19 inhibitor (compound 1, compound 2 or compound 3).

FIG. 1 shows results about the proportion of insulin-positive and NKX6.1-positive cells and the proportion of insulin-positive and NKX6.1-negative cells obtained by treatment with a medium for induction of differentiation containing ALK5 inhibitor II (10 μM) or a predetermined concentration of the CDK8/19 inhibitor (compound 1, compound 2 or compound 3) or containing neither ALK5 inhibitor II nor the CDK8/19 inhibitor. FIG. 2 shows results of flow cytometry of the cell population obtained using ALK5 inhibitor II (10 μM), 0.3 μM of compound 1, 3 nM of compound 2, or 0.1 μM of compound 3.

It was confirmed that when the medium for induction of differentiation contains the CDK8/19 inhibitor, a cell population can be produced in which the proportion of the insulin-positive and NKX6.1-positive cells of interest surpasses the proportion of the unintended insulin-positive and NKX6.1-negative cells.

Particularly, in the case of using 0.3 μM of compound 1, 3 nM of compound 2, or 0.1 μM of compound 3 as the CDK8/19 inhibitor, a cell population was able to be produced which had a higher proportion of the insulin-positive and NKX6.1-positive cells of interest than that in the case of using ALK5 inhibitor II (10 μM), which has heretofore been generally used in inducing the differentiation of a pancreatic progenitor cell population into an insulin-positive cell population.

In the case of using ALK5 inhibitor II, the proportion of the insulin-positive and NKX6.1-positive cells of interest was on the order of 33% in the obtained cell population. This proportion was equivalent or lower even when the concentration of the ALK5 inhibitor II added to the medium was elevated to 30 μM (data not shown).

On the other hand, treatment with the CDK8/19 inhibitor in the production process of inducing the differentiation of a pancreatic progenitor cell population into an insulin-positive cell population was confirmed to enhance the proportion of the cells of interest (insulin-positive and NKX6.1-positive cells) beyond 33% in the cell population.

The results described above demonstrated that a cell population is treated with the CDK8/19 inhibitor instead of ALK5 inhibitor II in the process of inducing the differentiation of a pancreatic progenitor cell population into an insulin-positive cell population, whereby an insulin-positive cell population comprising the cells of interest (insulin-positive and NKX6.1-positive cells) at a higher proportion than that of a conventional method can be produced.

The invention claimed is:

1. A method for producing an insulin-positive cell population, comprising differentiating, in a medium comprising a CDK8/19 inhibitor, (i) a pancreatic progenitor cell population in a step of inducing a differentiation of pancreatic progenitor cells into endocrine progenitor cells and/or (ii) an endocrine progenitor cell population in a step of inducing a differentiation of endocrine progenitor cells into insulin-positive cells.

2. The method according to claim 1, wherein the medium does not comprise an ALK5 inhibitor.

3. The method according to claim 1, wherein $IC_{50}$ of the CDK8/19 inhibitor against ALK5 is 1 μM or more.

4. The method according to claim 1, wherein the CDK8/19 inhibitor is one or more selected from the group consisting of diethyl (E)-(4-(3-(5-(4-fluorophenyl)-1-methyl-1H-pyrazol-4-yl)acrylamido)benzyl)phosphonate, 2-(4-(4-(isoquinolin-4-yl)phenyl)-1H-pyrazol-1-yl)-N,N-dimethylacetamide, 4-((2-(6-(4-methylpiperazine-1-carbonyl)naphthalen-2-yl)ethyl)amino)quinazoline-6-carbonitrile, 4-(4-(2,3-dihydrobenzo[b][1,4]dioxin-6-yl)-1H-pyrazol-3-yl)benzene-1,3-diol, 3-(2-(imidazo[1,2-b]pyridazin-6-ylthio)ethyl)-4-(naphthalen-1-ylsulfonyl)-3,4-dihydroquinoxalin-2 (1H)-one, and (E)-3-(4-(1-cyclopropyl-1H-pyrazol-4-yl)pyridin-3-yl)-N-(4-(morpholinomethyl)phenyl)acrylamide.

5. The method according to claim 1, wherein the pancreatic progenitor cell population or the endocrine progenitor cell population is a cell population produced by the induction of differentiation from pluripotent stem cells.

6. A differentiation medium for (i) a pancreatic progenitor cell population in a step of inducing a differentiation of pancreatic progenitor cells into endocrine progenitor cells and/or (ii) an endocrine progenitor cell population in a step of inducing a differentiation of endocrine progenitor cells into insulin-positive cells, comprising a CDK8/19 inhibitor.

7. The medium according to claim 6, wherein the medium does not comprise an ALK5 inhibitor.

8. The medium according to claim 6, wherein $IC_{50}$ of the CDK8/19 inhibitor against ALK5 is 1 μM or more.

9. The medium according to claim 6, wherein the CDK8/19 inhibitor is one or more selected from the group consisting of diethyl (E)-(4-(3-(5-(4-fluorophenyl)-1-methyl-1H-pyrazol-4-yl)acrylamido)benzyl)phosphonate, 2-(4-(4-(isoquinolin-4-yl)phenyl)-1H-pyrazol-1-yl)-N,N-dimethylacetamide, 4-((2-(6-(4-methylpiperazine-1-carbonyl)naphthalen-2-yl)ethyl)amino)quinazoline-6-carbonitrile, 4-(4-(2,3-dihydrobenzo[b][1,4]dioxin-6-yl)-1H-pyrazol-3-yl)benzene-1,3-diol, 3-(2-(imidazo[1,2-b]pyridazin-6-ylthio)ethyl)-4-(naphthalen-1-ylsulfonyl)-3,4-dihydroquinoxalin-2 (1H)-one, and (E)-3-(4-(1-cyclopropyl-1H-pyrazol-4-yl)pyridin-3-yl)-N-(4-(morpholinomethyl)phenyl)acrylamide.

10. The method according to claim 1, wherein the method comprises differentiating, in the medium comprising the CDK8/19 inhibitor, (i) the pancreatic progenitor cell population in the step of inducing differentiation of pancreatic progenitor cells into endocrine progenitor cells and (ii) the endocrine progenitor cell population in the step of inducing differentiation of endocrine progenitor cells into insulin-positive cells.

* * * * *